(12) United States Patent
Matsui et al.

(10) Patent No.: US 9,833,162 B2
(45) Date of Patent: Dec. 5, 2017

(54) ATRIAL FIBRILLATION DETECTION SYSTEM

(71) Applicant: UNION TOOL CO., Tokyo (JP)

(72) Inventors: Taishi Matsui, Tokyo (JP); Ryo Shinozaki, Tokyo (JP)

(73) Assignee: Union Tool Co., Tokyo (JP)

( * ) Notice: Subject to any disclaimer, the term of this patent is extended or adjusted under 35 U.S.C. 154(b) by 0 days.

(21) Appl. No.: 14/996,294

(22) Filed: Jan. 15, 2016

(65) Prior Publication Data

US 2016/0228020 A1 Aug. 11, 2016

(30) Foreign Application Priority Data

Feb. 5, 2015 (JP) .................................. 2015-021011

(51) Int. Cl.
*A61B 5/046* (2006.01)
*A61B 5/024* (2006.01)
(Continued)

(52) U.S. Cl.
CPC ............ *A61B 5/046* (2013.01); *A61B 5/0006* (2013.01); *A61B 5/02405* (2013.01);
(Continued)

(58) Field of Classification Search
CPC ...... A61N 1/395; A61B 5/046; A61B 5/02405
See application file for complete search history.

(56) References Cited

U.S. PATENT DOCUMENTS 8,121,675 B2 * 2/2012 Shaquer ................. A61B 5/046
600/515
2007/0073177 A1 3/2007 Kontothanassis et al.
(Continued)

FOREIGN PATENT DOCUMENTS

JP 7132118 A 5/1995
JP 11206727 A 8/1999
(Continued)

OTHER PUBLICATIONS

Communication dated Jun. 21, 2016, from the European Patent Office in counterpart European Application No. 16153134.8.
(Continued)

*Primary Examiner* — George Evanisko
(74) *Attorney, Agent, or Firm* — Sughrue Mion, PLLC

(57) ABSTRACT

Provided is an atrial fibrillation detection system which can reduce the burden on a test subject, with which it is possible to detect even paroxysmal atrial fibrillation, and which can be used in the home, contributing to early detection of atrial fibrillation. This atrial fibrillation detection system detects the presence of atrial fibrillation in a subject, and is provided with a heartbeat period measurement means that measures heartbeat periods of the heart; a normalized heartbeat period computation means that computes normalized heartbeat periods DR(N) from heartbeat periods of the heart measured by the heartbeat period measurement means; an abnormal normalized heartbeat period cumulation means that, from among a prescribed number of successive normalized heartbeat periods DR(N), adds up the count of abnormal normalized heartbeat periods that have an absolute value exceeding a normal heartbeat period value; and a comparison/determination means that compares the cumulative count of the abnormal normalized heartbeat periods and a normal cumulative count threshold value, and in the event that the cumulative count of the abnormal normalized heartbeat periods exceeds the normal cumulative count threshold value, determines that atrial fibrillation has occurred.

18 Claims, 11 Drawing Sheets

(51) Int. Cl.
*A61B 5/00* (2006.01)
*A61B 5/04* (2006.01)
*A61N 1/39* (2006.01)

(52) U.S. Cl.
CPC ...... *A61B 5/04012* (2013.01); *A61B 5/04014* (2013.01); *A61N 1/395* (2013.01)

(56) References Cited

U.S. PATENT DOCUMENTS

| | | |
|---|---|---|
| 2012/0101541 A1 | 4/2012 | Corbucci et al. |
| 2014/0031708 A1 | 1/2014 | Lo et al. |
| 2014/0330134 A1 | 11/2014 | Chon et al. |

FOREIGN PATENT DOCUMENTS

| | | |
|---|---|---|
| JP | 20086005 A | 1/2008 |
| JP | 2009-89883 A | 4/2009 |
| JP | 2012183168 A | 9/2012 |
| JP | 2013-55982 A | 3/2013 |
| WO | 03077755 A1 | 9/2003 |
| WO | 2008128034 A1 | 10/2008 |

OTHER PUBLICATIONS

Jurgen R. Schaefer et al. :Improved Detection of Paroxysmal Atrial Fibrillation Utilizing a Software-Assisted Electrocardiogram Approach Plos One, vol. 9 No. 2; Feb. 28, 2014; e89328, pp. 1-7.
Communication dated Dec. 1, 2016, from the Japanese Patent Office in counterpart application No. 2015-021011.

\* cited by examiner

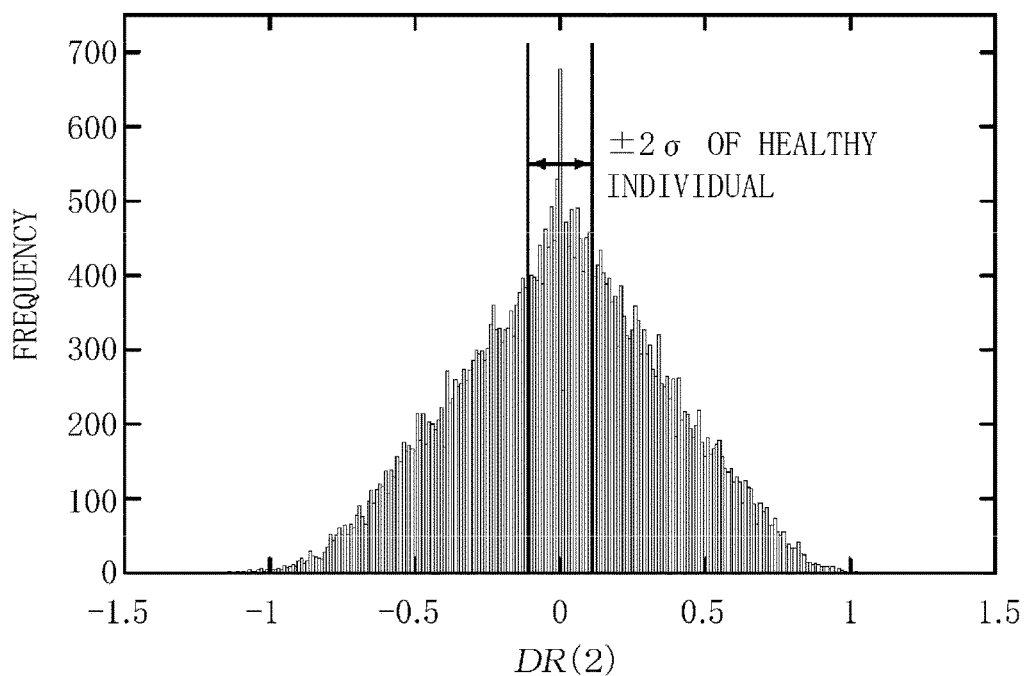
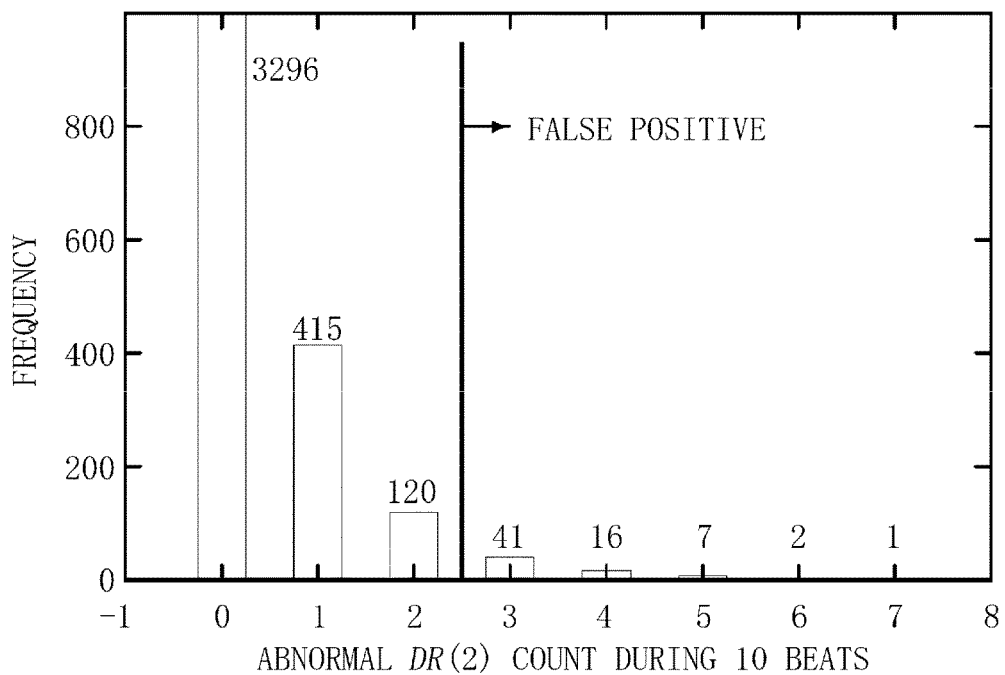

ATRIAL FIBRILLATION DETECTION SYSTEM

BACKGROUND OF THE INVENTION

Technical Field

The present invention relates to an atrial fibrillation detection system.

Background Art

Atrial fibrillation refers to a condition in which the atria twitch finely and cannot contract sufficiently, due to irregular and rapid stimulation throughout the atria. Meanwhile, since some stimulation of the atria travels through the atrioventricular node, the ventricles contract at irregular intervals, irrespective of the sinus rhythm. Thus, because the ventricles contract, albeit irregularly, and there is no marked loss of coronary function, many people fail to notice the symptoms of atrial fibrillation. It is estimated that there are about 1,000,000 patients suffering from atrial fibrillation within Japan, but it is thought that if people who fail to notice the symptoms were included, the number of patients would be far greater.

Since, the atria cannot contract sufficiently under atrial fibrillation, blood tends to pool within the atria, producing clots, leading to the possibility that such a clot may be transported to the brain, causing a cerebral infarction. Therefore, patients with atrial fibrillation are said to be about five times more likely to have a cerebral infarction than individuals without symptoms.

Because blood clots produced by atrial fibrillation are large in size, in many instances large blood vessels of the brain become obstructed. For this reason, a cerebral infarction that is caused by atrial fibrillation can inflict wide-ranging damage to the brain, making a prognosis that the individual will be left with an impediment severe enough to require nursing care highly likely. Nursing care may impose physical, psychological, and economic burdens on the family providing assistance, and is thought to impose a large economic burden on society as well.

While full recovery from atrial fibrillation may prove possible by reducing clot formation through the administration of drugs, or by catheter ablation, early detection is necessary to do so. However, as mentioned above, atrial fibrillation in many cases does not produce subjective symptoms. Moreover, in paroxysmal cases, the disorder may not be discovered by an EKG exam during a routine checkup or hospital visit.

Research has been carried out with the goal of using the heartbeat period to distinguish atrial fibrillation. For example, one such method involves calculating the distribution of the difference ΔR in adjacent heartbeat periods for a healthy individual and an atrial fibrillation patient, respectively, and automatically detecting atrial fibrillation by the Kolmogorov-Smirnov test. However, this method requires that heartbeat period values be taken over an extended period in order to obtain the ΔR distribution, imposing a burden on the test subjects. Moreover, it is possible that paroxysmal atrial fibrillation occurring within a brief time interval will not be detected.

Another method distinguishes atrial fibrillation based on a standard deviation obtained from a heartbeat period distribution (Patent Document 1). However, the technique disclosed in Patent Document 1 also requires heartbeat periods to be calculated, and therefore requires that heartbeat period values be taken over an extended period.

A further method distinguishes the condition through frequency analysis of heartbeat period fluctuations (Patent Document 2), but requires heartbeat period values measured continuously over several minutes for the purpose of frequency analysis, and it is possible that paroxysmal atrial fibrillation will not be detected.

RELATED ART DOCUMENTS

Patent Documents

[Patent Document 1] Japanese Laid-open Patent Application 2009-89883

[Patent Document 2] Japanese Laid-open Patent Application 2013-55982

SUMMARY OF THE INVENTION

Problems the Invention is Intended to Solve

With the foregoing in view, it is an object of the present invention to provide a novel atrial fibrillation detection system with which it is possible to detect (symptoms of) atrial fibrillation using only heartbeat period values measured over a brief time period, so that the burden on the test subject can be reduced, and with which it is possible to detect even paroxysmal atrial fibrillation; and moreover to accomplish this using a compact measuring device for measuring only heartbeat periods of the heart, thus making use in the home possible, and contributing to early detection of atrial fibrillation.

Means for Solving these Problems

A summary of the present invention will be described with reference to the accompanying drawings.

The present invention relates to an atrial fibrillation detection system for detecting the presence of atrial fibrillation in a subject, wherein the atrial fibrillation detection system is characterized by being provided with heartbeat period measurement means that measures heartbeat periods of the heart; normalized heartbeat period computation means that computes normalized heartbeat periods DR(N), represented by the following equation (1), where $R_n$ is a time series of heartbeat periods of the heart, from heartbeat periods of the heart that were measured by the heartbeat period measurement means; abnormal normalized heartbeat period cumulation means that, from among a prescribed number of successive normalized heartbeat periods DR(N), adds up the count of abnormal normalized heartbeat periods that have an absolute value exceeding a normal heartbeat period value; and comparison/determination means that compares the cumulative count of the abnormal normalized heartbeat periods and a normal cumulative count threshold value, and in the event that the cumulative count of the abnormal normalized heartbeat periods exceeds the normal cumulative count threshold value, determines that atrial fibrillation has occurred.

$$DR(N)_n = \frac{N(R_{n-1} - R_n)}{\sum_{k=n-N+1}^{n} R_k} \quad (1)$$

N is an integer equal to 1 or greater, subscript n is a time series, and n signifies the past with respect to n+1.

The present invention also relates to an atrial fibrillation detection system according to the first aspect, wherein the atrial fibrillation detection system is characterized by being provided with premature ventricular contraction exclusion means that excludes from the normalized heartbeat periods those normalized heartbeat periods that relate to premature ventricular contractions.

The present invention also relates to an atrial fibrillation detection system according to the second aspect, wherein the atrial fibrillation detection system is characterized in that the premature ventricular contraction exclusion means is configured to exclude normalized heartbeat periods that relate to premature ventricular contractions, by the following method.

From among the normalized heartbeat periods $DR(N)_i$ from a time series $R_i$ of heartbeat periods of the heart, a normalized heartbeat period $DR(N)i$ that satisfies the following equations (2) and (3) is retrieved, then $DR(N)i$ and two values $DR(N)_{i+1}$ and $DR(N)_{i+2}$ successive thereto are excluded from the retrieved normalized heartbeat period $DR(N)_i$.

$$|DR(N)_i| > T_P \quad (2)$$

$$\frac{|R_i + R_{i+1} - 2\overline{R}_{i-1}(M)|}{2\overline{R}_{i-1}(M)} < 2T_N \quad (3)$$

$T_P$ and $T_N$ are prescribed threshold values that satisfy the relationships $T_P>0$ and $T_N>0$, subscript i is a time series, and i signifies the past with respect to i+1.

$R_i$ bar (X) in equation (3) is represented by the following equation (4).

$$\overline{R}_i(X) = \frac{1}{X}\sum_{k=i-X+1}^{i} R_k \quad (4)$$

M and X are integers equal to 1 or greater.

The present invention also relates to an atrial fibrillation detection system according to the first aspect, wherein the atrial fibrillation detection system is characterized by being provided with a premature atrial contraction exclusion means that excludes from the normalized heartbeat periods those normalized heartbeat periods that relate to premature atrial contractions.

The present invention also relates to an atrial fibrillation detection system according to the second aspect, wherein the atrial fibrillation detection system is characterized by being provided with a premature atrial contraction exclusion means that excludes from the normalized heartbeat periods those normalized heartbeat periods that relate to premature atrial contractions.

The present invention also relates to an atrial fibrillation detection system according to the third aspect, wherein the atrial fibrillation detection system is characterized by being provided with a premature atrial contraction exclusion means that excludes from the normalized heartbeat periods those normalized heartbeat periods that relate to premature atrial contractions.

The present invention also relates to an atrial fibrillation detection system according to the fourth aspect, wherein the atrial fibrillation detection system is characterized in that the premature atrial contraction exclusion means is configured to exclude normalized heartbeat periods that relate to premature atrial contractions, by the following method.

From among the normalized heartbeat periods $DR(N)_i$ from a time series $R_i$ of heartbeat periods of the heart, a normalized heartbeat period $DR(N)_i$ that satisfies the following equations (5) and (6) is retrieved. Then $DR(N)_i$ and the value $DR(N)_{i+1}$ successive thereto are excluded from the retrieved normalized heartbeat period $DR(N)_i$.

$$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

$T_N$ and $T_A$ are prescribed threshold values that satisfy the relationships $T_N>0$ and $-T_N \leq T_A \leq 0$, subscript i is a time series, and i signifies the past with respect to i+1.

M is an integer equal to 1 or greater, and K is an integer equal to 0 or greater.

$R_i$ bar (X) in equations (5) and (6) is represented by the following equation (7) when X is an integer equal to 1 or greater, and by the following equation (8) when X=0.

$$\overline{R}_i(X) = \frac{1}{X}\sum_{k=i-X+1}^{i} R_k \quad (7)$$

$$\overline{R}_i(0) = 0 \quad (8)$$

The present invention also relates to an atrial fibrillation detection system according to the fifth aspect, wherein the atrial fibrillation detection system is characterized in that the premature atrial contraction exclusion means is configured to exclude normalized heartbeat periods that relate to premature atrial contractions, by the following method.

From among the normalized heartbeat periods $DR(N)_i$ from a time series $R_i$ of heartbeat periods of the heart, a normalized heartbeat period $DR(N)_i$ that satisfies the following equations (5) and (6) is retrieved. Then $DR(N)_i$ and the value $DR(N)_{i+1}$ successive thereto are excluded from the retrieved normalized heartbeat period $DR(N)_i$.

$$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

$T_N$ and $T_A$ are prescribed threshold values that satisfy the relationships $T_N>0$ and $-T_N \leq T_A \leq 0$, subscript i is a time series, and i signifies the past with respect to i+1.

M is an integer equal to 1 or greater, and K is an integer equal to 0 or greater.

$R_i$ bar (X) in equations (5) and (6) is represented by the following equation (7) when X is an integer equal to 1 or greater, and by the following equation (8) when X=0.

$$\overline{R}_i(X) = \frac{1}{X}\sum_{k=i-X+1}^{i} R_k \quad (7)$$

$$\overline{R}_i(0) = 0 \quad (8)$$

The present invention also relates to an atrial fibrillation detection system according to the sixth aspect, wherein the atrial fibrillation detection system is characterized in that the premature atrial contraction exclusion means is configured to exclude normalized heartbeat periods that relate to premature atrial contractions, by the following method.

From among the normalized heartbeat periods $DR(N)_i$ from a time series $R_i$ of heartbeat periods of the heart, a normalized heartbeat period $DR(N)_i$ that satisfies the following equations (5) and (6) is retrieved. Then $DR(N)_i$ and the value $DR(N)_{i+1}$ successive thereto are excluded from the retrieved normalized heartbeat period $DR(N)_i$.

$$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

$T_N$ and $T_A$ are prescribed threshold values that satisfy the relationships $T_N > 0$ and $-T_N \le T_A \le 0$, subscript i is a time series, and i signifies the past with respect to i+1.

M is an integer equal to 1 or greater, and K is an integer equal to 0 or greater.

$R_i$ bar (X) in equations (5) and (6) is represented by the following equation (7) when X is an integer equal to 1 or greater, and by the following equation (8) when X=0.

$$\overline{R}_i(X) = \frac{1}{X} \sum_{k=i-X+1}^{i} R_k \quad (7)$$

$$\overline{R}_i(0) = 0 \quad (8)$$

The present invention also relates to an atrial fibrillation detection system according to the first aspect, wherein the atrial fibrillation detection system is characterized in that the normalized heartbeat period computation means is configured to compute a normalized heartbeat period $DR(2)_n$, represented by the following equation (9), from the heartbeat periods.

$$DR(2)_n = \frac{2(R_{n-1} - R_n)}{R_{n-1} + R_n} \quad (9)$$

The present invention also relates to an atrial fibrillation detection system according to the first aspect, wherein the atrial fibrillation detection system is characterized by comprising a sensor for heartbeat measurement provided with the heartbeat period measurement means, and an analyzer provided with the normalized heartbeat period computation means, the abnormal normalized heartbeat period cumulation means, and the comparison/determination means.

The present invention also relates to an atrial fibrillation detection system according to the tenth aspect, wherein the atrial fibrillation detection system is characterized by comprising a sensor for heartbeat measurement provided with the heartbeat period measurement means, and an analyzer provided with the normalized heartbeat period computation means, the abnormal normalized heartbeat period cumulation means, and the comparison/determination means.

The present invention also relates to an atrial fibrillation detection system according to the eleventh aspect, wherein the atrial fibrillation detection system is characterized in that the sensor is provided with a heartbeat period storage means for storing heartbeat periods measured by the heartbeat period measurement means, or provided with heartbeat period transmission means for transmitting to an analyzer the measured heartbeat periods, the system being configured such that atrial fibrillation is detected by inputting the heartbeat periods measured using the sensor to the analyzer via the heartbeat period storage means or the heartbeat period transmission means.

The present invention also relates to an atrial fibrillation detection system according to the twelfth aspect, wherein the atrial fibrillation detection system is characterized in that the sensor is provided with a heartbeat period storage means for storing heartbeat periods measured by the heartbeat period measurement means, or provided with heartbeat period transmission means for transmitting to an analyzer the measured heartbeat periods, the system being configured such that atrial fibrillation is detected by inputting the heartbeat periods measured using the sensor to the analyzer via the heartbeat period storage means or the heartbeat period transmission means.

Effect of the Invention

The present invention, by being configured as described above, makes it possible to detect (symptoms of) atrial fibrillation using only heartbeat period values measured over a brief time period, so that the burden on the test subject can be reduced, and makes it possible to detect even paroxysmal atrial fibrillation, and moreover to accomplish this using a compact measuring device for measuring only heartbeat periods of the heart, thus making use in the home possible, and contributing to early detection of atrial fibrillation.

BRIEF DESCRIPTION OF THE DRAWINGS

FIG. 5 is a graph showing a frequency distribution of DR(2) in an atrial fibrillation patient;

FIG. 6 is a graph showing a distribution of abnormal DR(2) count during 10 beats in a healthy individual;

DETAILED DESCRIPTION OF THE INVENTION

Figure 1:
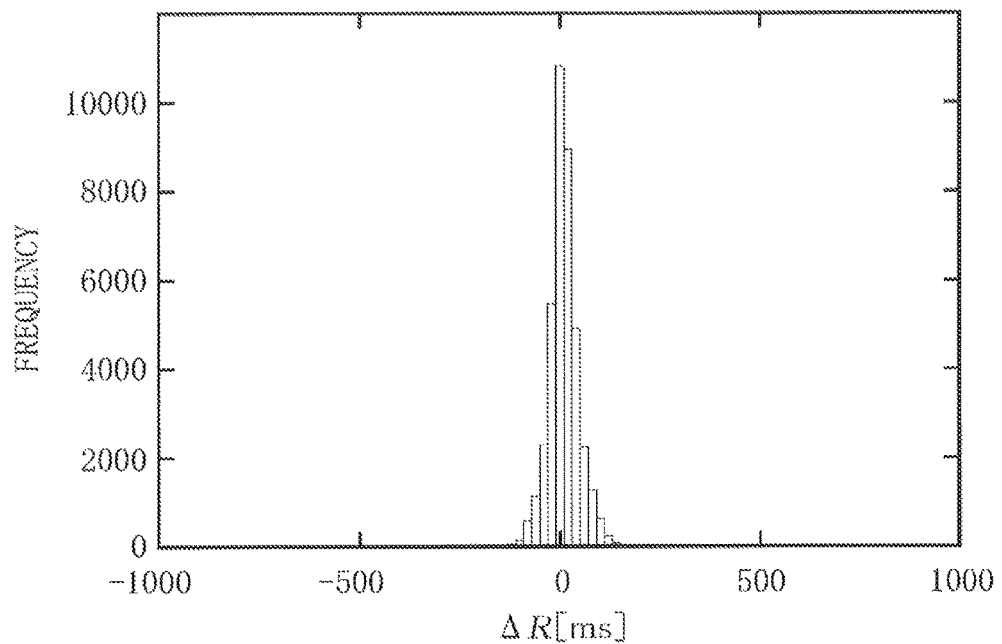
FIG. 1 is a graph showing a frequency distribution of ΔR in a healthy individual.

The presently preferred embodiments of the present invention are described in brief below, to show the operation of the present invention on the basis of the drawings.

It has been verified that a determination of atrial fibrillation can be made in cases in which, from among a prescribed number (as discussed below, about 20 at the most) of normalized heartbeat periods DR(N), those having absolute values that exceed a prescribed normal heartbeat period threshold value are counted as abnormal normalized heartbeat periods, and the count of these abnormal normalized heartbeat periods is found to exceed a prescribed normal cumulative count threshold value. It is therefore easy to detect whether or not a subject has atrial fibrillation.

Moreover, it is possible to detect symptoms of atrial fibrillation from heartbeat period values measured over a brief time period, commensurately reducing the burden on the test subject, and it is also possible to detect paroxysmal atrial fibrillation occurring within a brief time period.

Additionally, normalized heartbeat periods DR(N) can be computed from the heartbeat periods of a subject, thereby obviating the need to employ a specialized device of the type normally used to detect paroxysmal atrial fibrillation, such as a Holter monitor electrocardiograph, twelve-lead resting electrocardiograph, or other such relatively bulky device for which the electrode locations are strictly specified, so that normalized heartbeat periods DR(N) can be calculated from heartbeat periods measured, for example, with a heart rate meter designed to be stuck to the chest, a wristband type plethysmograph, or other compact measurement device that can easily be used at home, and by the procedure described above, it can be detected whether or not there is atrial fibrillation.

Embodiments

A specific embodiment of the present invention will be described on the basis of the drawings.

The present embodiment is an atrial fibrillation detection system 1 for detecting the presence of atrial fibrillation in a subject, provided with a heartbeat period measurement means 4 that measures heartbeat periods of the heart; a normalized heartbeat period computation means 7 that computes normalized heartbeat periods DR(N), represented by the preceding equation (1), where $R_n$ is a time series of heartbeat periods of the heart, from heartbeat periods of the heart that were measured by the heartbeat period measurement means 4; an abnormal normalized heartbeat period cumulation means 10 that adds up the count of abnormal normalized heartbeat periods having an absolute value that exceeds a normal heartbeat period value, from among a prescribed number of successive normalized heartbeat periods DR(N); and a comparison/determination means 12 that compares the cumulative count of the abnormal normalized heartbeat periods and a normal cumulative count threshold value, and in the event that the cumulative count of the abnormal normalized heartbeat periods exceeds the normal cumulative count threshold value, determines that atrial fibrillation has occurred.

Figure 17:
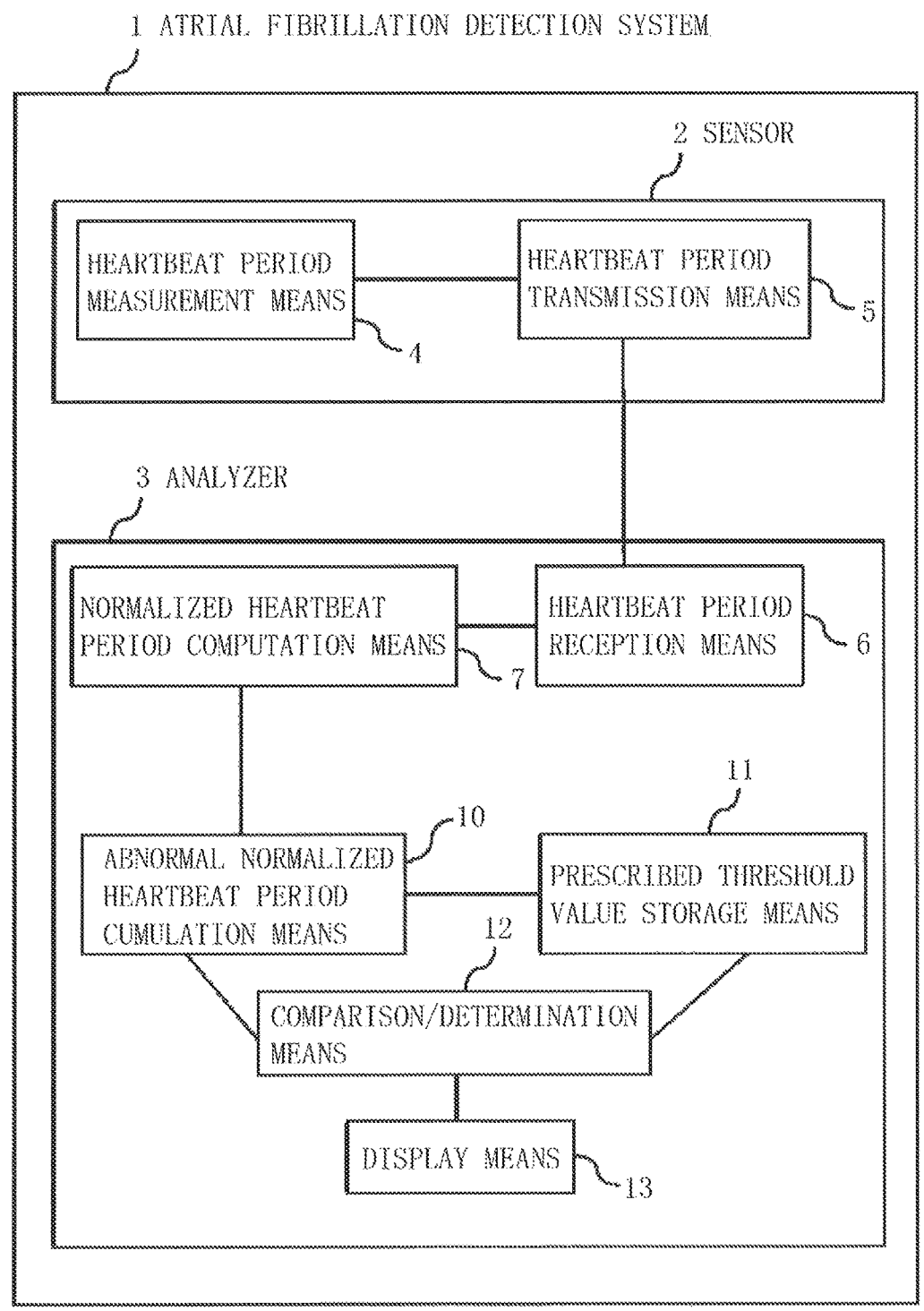
FIG. 17 is a diagrammatic illustration of configuration of the present embodiment.

More specifically, as shown in FIG. 17, the present embodiment is constituted by a sensor 2 for heartbeat period measurement, which is provided with the heartbeat period measurement means 4; and an analyzer 3 which is provided with the normalized heartbeat period computation means 7, the abnormal normalized heartbeat period cumulation means 10, and the comparison/determination means 12.

Each part is described in specific terms below.

The sensor 2 is provided with the heartbeat period measurement means 4, and with a heartbeat period transmission means 5 for transmitting the heartbeat period data measured by the heartbeat period measurement means 4, to a heartbeat period reception means 6 of the analyzer 3.

The heartbeat period measurement means 4 is configured, for example, to use a microcomputer or the like to measure the heartbeat period from the interval between an R wave and another neighboring R wave, or from the interval between an S wave and another neighboring S wave, in an electrocardiogram based on changes in voltage obtained from electrodes. Consequently, where a compact sensor is stuck to the skin via electrodes, the sensor can be hidden beneath the clothing, and measurements can be performed without hampering daily activities.

Optionally, the heartbeat period measurement means 4 may be configured, for example, to measure the pulse wave from reflected infrared light, and to measure the heartbeat periods from the peak intervals thereof, or the like. In this case, it will suffice simply to fasten the sensor to the earlobe, the wrist, the arm, or the like with a clip or band, for ease of wear. Configurations in which heartbeat periods are measured by electrical processing of cardiac sound or pulse sound are also acceptable. In this case, it will be possible to house the sensor inside a stethoscope or blood pressure gauge, so as to promote widespread use.

The heartbeat period measurement means 4 transfers the measured heartbeat period data to the heartbeat period transmission means 5.

The heartbeat period transmission means 5 transfers the heartbeat period data received from the heartbeat period measurement means 4 to the heartbeat period reception means 6 which is provided to the analyzer 3. In the present embodiment, a wireless arrangement employing radio waves or light is adopted as the transfer method. In this case, the sensor can be more compact, and the subject can measure heartbeat periods without hindering daily activities. Alternatively, a wired arrangement may be adopted as the transfer method, employing, for example, wiring on a printed circuit board, an electrical cable, or an optical cable. This is appropriate in cases of building a system in which the sensor and analyzer are integrated. It is also possible to employ phone lines, the internet, or other public communications lines, in which case it will be possible to detect atrial fibrillation of the subject remotely.

The analyzer 3 is provided with the heartbeat period reception means 6, the normalized heartbeat period computation means 7, the abnormal normalized heartbeat period cumulation means 10, a prescribed threshold value storage means 11, the comparison/determination means 12, and a display means 13. The analyzer 3 is an electronic calculator or measuring device for performing a series involving computation, comparison, and display; a dedicated device, PC, tablet computer, smartphone, mobile phone, or the like provided with each of the aforementioned means can be adopted.

The heartbeat period reception means 6 receives heartbeat period data from the heartbeat period transmission means 5 of the sensor 2, and transfers the data to the normalized heartbeat period computation means 7.

The normalized heartbeat period computation means 7 computes normalized heartbeat periods by a prescribed method, and transfers the normalized heartbeat periods to the abnormal normalized heartbeat period cumulation means 10.

The abnormal normalized heartbeat period cumulation means 10 makes reference to a normal heartbeat period threshold value, stored in the prescribed threshold value storage means 11, for recognizing abnormal normalized heartbeat periods, and from the normalized heartbeat periods in intervals containing prescribed numbers of heartbeats, takes a cumulative count of those that have an absolute value that exceeds the normal heartbeat period threshold value, designating these as abnormal normalized heartbeat periods; and then transfers the abnormal normalized heartbeat period count per prescribed heart rate interval to the comparison/determination means 12.

The comparison/determination means 12, making reference to a normal cumulative count threshold value per prescribed heart rate interval, which is stored in the prescribed threshold value storage means 11, detects any prescribed heart rate interval in which the abnormal normalized heartbeat period count for the prescribed heart rate interval exceeds the normal cumulative count threshold value, as being a point of occurrence of atrial fibrillation, and transfers the results to the display means 13.

The display means 13 displays whether or not atrial fibrillation has been detected. As the display means 13, there can be employed a display for displaying text, images, or the like. In this case, a time series of heartbeat periods can be displayed, together with the time, as a graph, to produce an easy-to-understand display indicating when the heartbeat period in which atrial fibrillation occurred was observed. Light, sound, or vibration can also be employed as the display means 13. In this case, immediate notification that atrial fibrillation has occurred can be provided. For example, an LED can be employed as light source, a buzzer or earphone as a sound source, or a motor as a vibration source.

Figure 18:
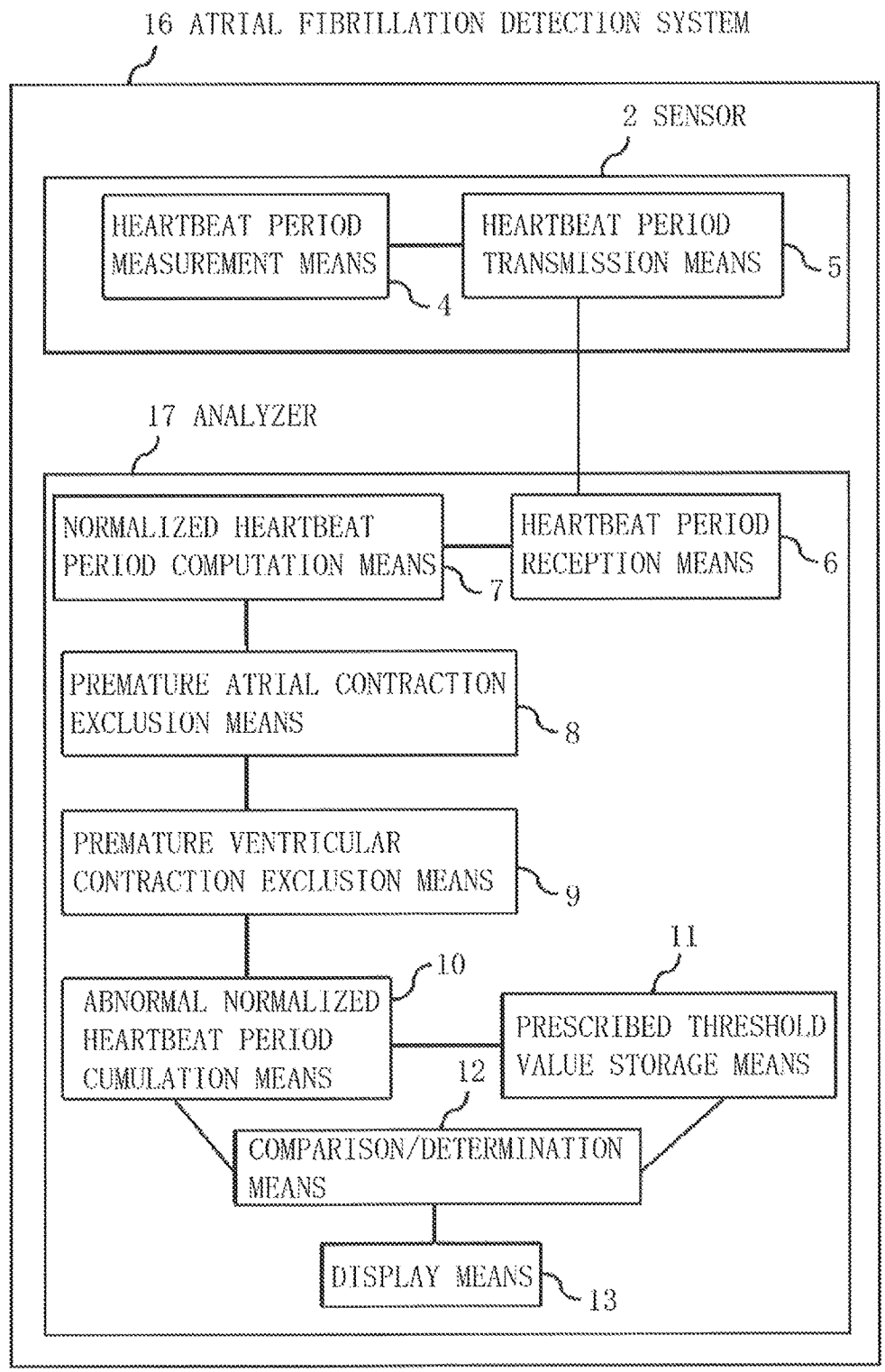
FIG. 18 is a diagrammatic illustration of configuration of the present embodiment.

With the aforedescribed configuration (the atrial fibrillation detection system 1), it is possible to detect atrial fibrillation; however, in the present embodiment, in order to further improve the detection accuracy, a configuration like the atrial fibrillation detection system 16 depicted in FIG. 18, in which an analyzer 17 is further provided with a premature atrial contraction exclusion means 8 for excluding normalized heartbeat periods that relate to premature atrial contractions, and a premature ventricular contraction exclusion means 9 for excluding normalized heartbeat periods that relate to premature ventricular contractions, is acceptable. Detection accuracy can be improved even with configuration provided only with either the premature atrial contraction exclusion means 8 or the premature ventricular contraction exclusion means 9.

Specifically, the premature atrial contraction exclusion means 8 is configured to retrieve, from the normalized heartbeat periods $DR(N)_i$ from a time series $R_i$ of heartbeat periods of the heart, normalized heartbeat periods $DR(N)_i$ that satisfy the preceding equations (5) and (6), and to then exclude $DR(N)_i$ and $DR(N)_{i+1}$ successive thereto from the retrieved normalized heartbeat periods $DR(N)_i$, to exclude normalized heartbeat periods that relate to premature atrial contractions.

The premature ventricular contraction exclusion means 9 is configured to retrieve, from the normalized heartbeat periods $DR(N)_i$ from a time series $R_i$ of heartbeat periods of the heart, a normalized heartbeat period $DR(N)_i$ that satisfies the preceding equations (2) and (3), and then to exclude the $DR(N)_i$ and the two values $DR(N)_{i+1}$ and $DR(N)_{i+2}$ successive thereto from the retrieved normalized heartbeat period $DR(N)_i$, to exclude normalized heartbeat periods that relate to premature ventricular contractions.

In cases in which the premature atrial contraction exclusion means 8 and the premature ventricular contraction exclusion means 9 are provided, the process is as follows.

From among the normalized heartbeat periods that were calculated by the normalized heartbeat period computation means 7, normalized heartbeat periods that relate to premature atrial contractions are excluded in accordance with a prescribed procedure by the premature atrial contraction exclusion means 8.

In accordance with a prescribed procedure, the premature ventricular contraction exclusion means 9 excludes normalized heartbeat periods that relate to premature ventricular contractions from the normalized heartbeat periods that were calculated by the normalized heartbeat period computation means 7.

The procedure of either the premature atrial contraction exclusion means 8 or the premature ventricular contraction exclusion means 9 may take place first. After normalized heartbeat periods that relate to premature atrial contractions and normalized heartbeat periods that relate to premature ventricular contractions have been excluded, the normalized heartbeat periods are transferred to the abnormal normalized heartbeat period computation means 10, and processed by the abnormal normalized heartbeat period computation means 10 and the comparison/determination means 12 as mentioned above.

Figure 19:
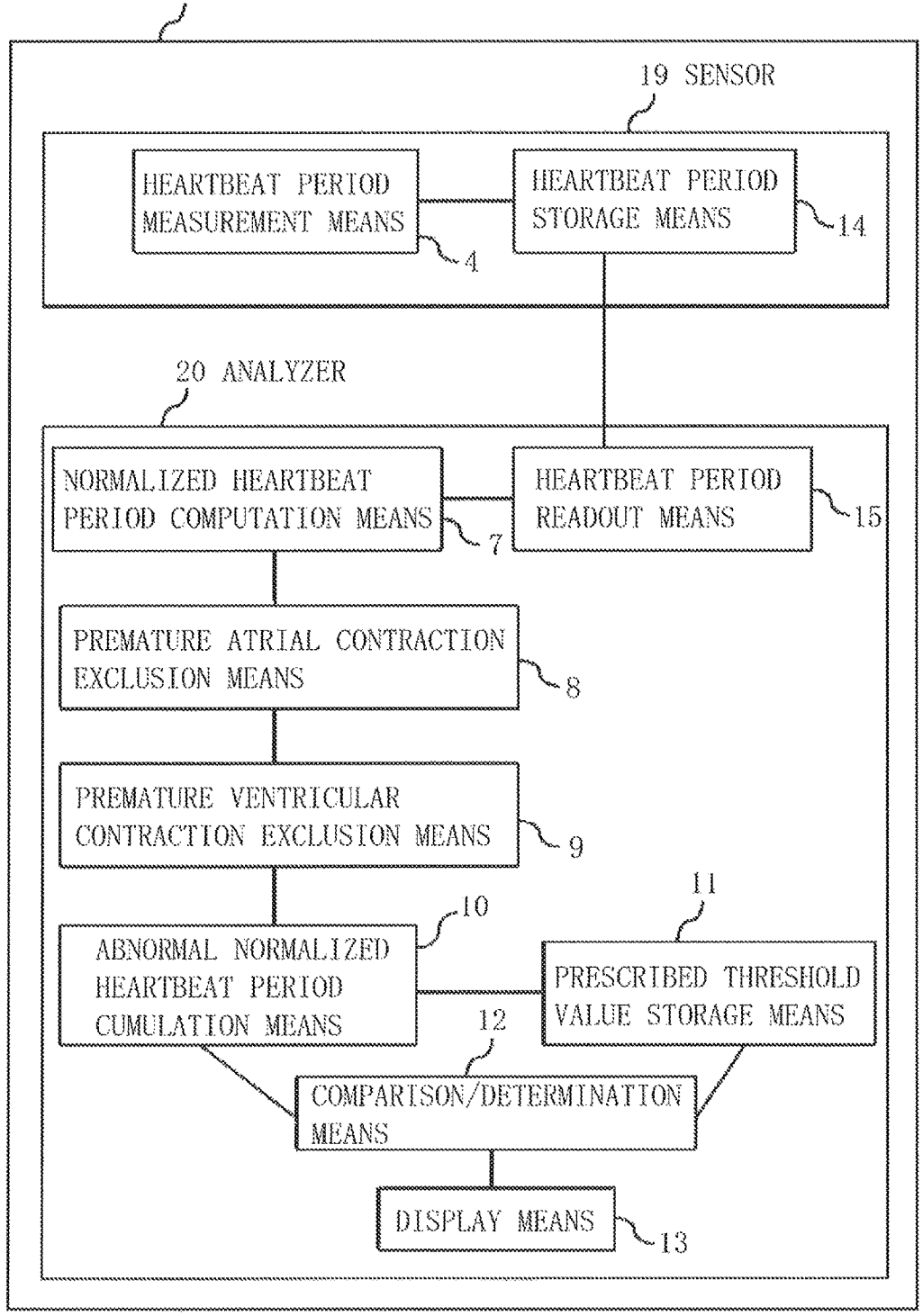
FIG. 19 is a diagrammatic illustration of configuration of another example.

In another acceptable configuration like that in the additional example depicted in FIG. 19 (atrial fibrillation detection system 18), a sensor 19 is provided with a heartbeat period storage means 14 in place of the heartbeat period transmission means 5 of the present embodiment, and an analyzer 20 is provided with a heartbeat period readout means 15 in place of the heartbeat period reception means 6 of the present embodiment. The heartbeat period storage means 14 of the sensor 19 stores the heartbeat periods that have been measured by the heartbeat period measurement means 4. Specifically, a tape, semiconductor memory, or the like can be adopted. Unlike a Holter monitor electrocardiograph, there is no need to store electrocardiographic complexes, and in cases in which a semiconductor memory is employed as the heartbeat period storage means 14, an extremely compact memory having low power consumption can be employed, thereby making possible a compact and lightweight configuration for the sensor 19, so as not to impose a burden on the test subject. The heartbeat period readout means 15 of the sensor 20 reads out the heartbeat periods stored in the heartbeat period storage means 14 of the sensor 19, and transfers the heartbeat periods to the normalized heartbeat period computation means 7. As to the timing for readout, readout may take place in real time while measurement is ongoing, or readout in bulk may take place after a prescribed measurement duration. The route by which the heartbeat periods are read out from the heartbeat period storage means 14 may be wired or wireless. In the case of a wired arrangement, for example, USB or RS-232C can be employed, for rapid and reliable readout of heartbeat periods. In the case of a wireless arrangement, either light or radio waves are acceptable, and heartbeat periods can be easily read out by the user, providing a more practical system.

The reason for adopting a method that employs the aforementioned equations (1) to (9) when detecting atrial fibrillation is discussed in detail below.

ΔR Distributions of Healthy Individuals and Atrial Fibrillation Patients

Figure 2:
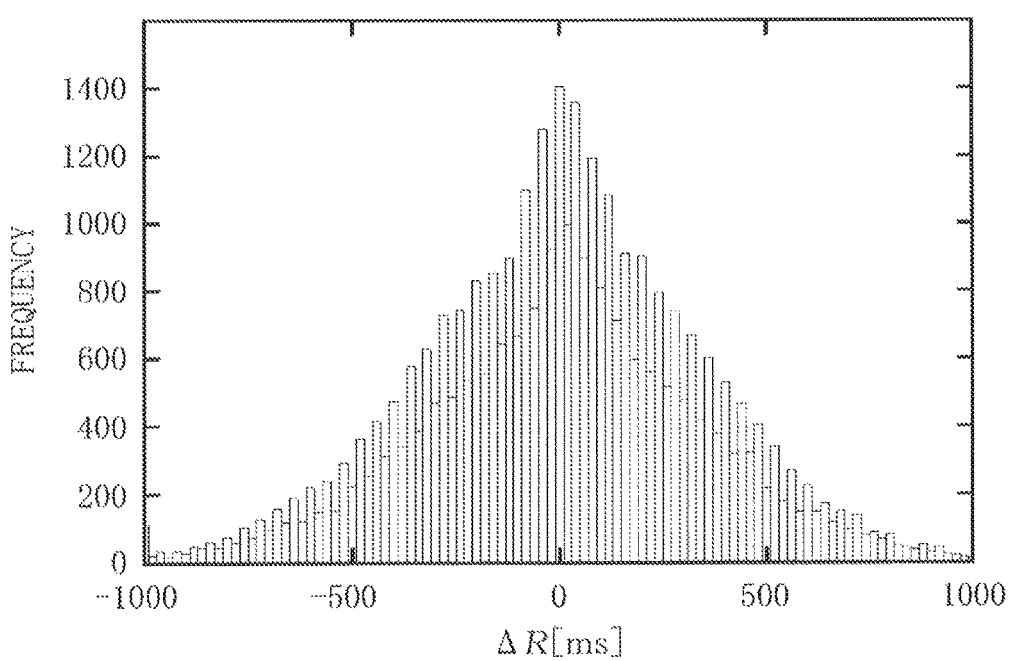
FIG. 2 is a graph showing a frequency distribution of ΔR in an atrial fibrillation patient.

From the heartbeat periods respectively recorded over two hours in four healthy individuals and five atrial fibrillation patients, distributions of the difference ΔR between neighboring heartbeat periods were examined. The ΔR distributions of the healthy individuals and the atrial fibrillation patients are shown respectively in FIG. 1 and FIG. 2. The horizontal axis is a scale having a scale interval of 10 ms, and the vertical axis is frequency. A simple glance suffices to appreciate that the distribution is wider for the atrial fibrillation patients than for the healthy individuals. It may be thought that atrial fibrillation can be detected when large ΔR values are counted. However, this difference in the distributions cannot simply be employed to detect atrial fibrillation. The reason is that the magnitude of fluctuation of heartbeat periods differs depending on the average heart rate, i.e., the average heartbeat period. For example, during exercise, a person's heart rate is high, i.e., the heartbeat period is small, but fluctuation of the heartbeat period at this time is small. Consequently, it is necessary to normalize ΔR by some heartbeat period value. First, the distribution of normalized heartbeat periods, defined by the following equation (10), for the atrial fibrillation patients was examined.

$$DR(1)_n = \frac{R_{n-1} - R_n}{R_{n-1}} \tag{10}$$

Figure 3:
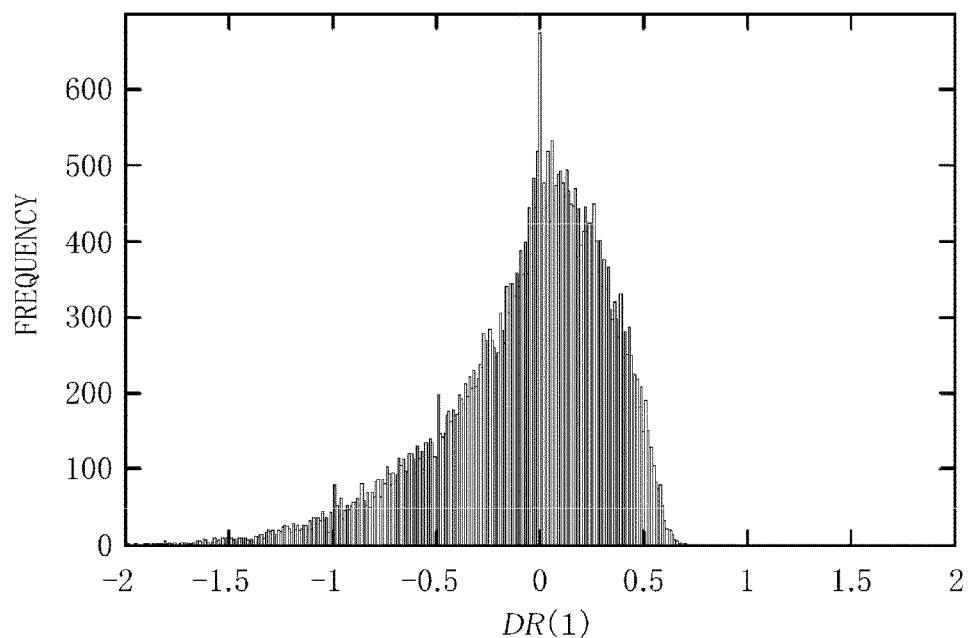
FIG. 3 is a graph showing a frequency distribution of DR(1) in an atrial fibrillation patient.

Here, R is the heartbeat period, subscript n is a time series, and n signifies the past with respect to n+1. The distribution of $DR(1)_n$ is plotted in FIG. 3. The horizontal axis is a scale having a scale interval of 0.01, and the vertical axis is frequency. Because the distribution is asymmetrical, $DR(1)_n$ is unsuited to detecting atrial fibrillation. A case of using the definition $$DR(1)_n = \frac{R_{n-1} - R_n}{R_n} \tag{11}$$

was examined as well, but as in FIG. 3, an asymmetrical result for the distribution was obtained. Next, distributions for a healthy individual and an atrial fibrillation patient obtained using normalized heartbeat periods defined by the following equation (12) (the following equation (12) is the same as equation (9)) were examined.

$$DR(2)_n = \frac{2(R_{n-1} - R_n)}{R_{n-1} + R_n} \tag{12}$$

Figure 4:
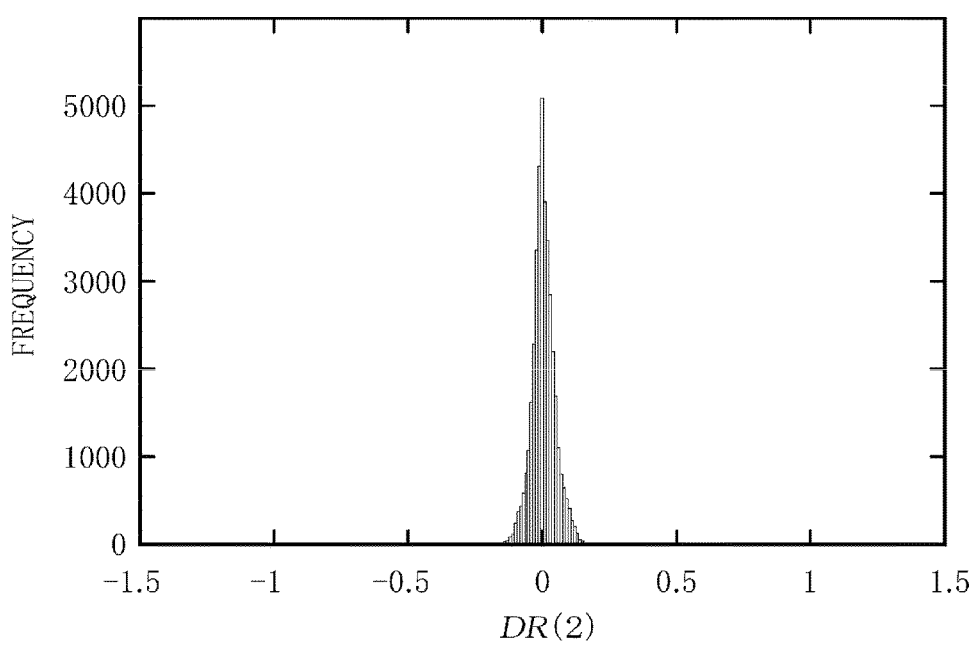
FIG. 4 is a graph showing a frequency distribution of DR(2) in a healthy individual.

These are shown respectively in FIG. 4 and FIG. 5. The horizontal axis is a scale having a scale interval of 0.01, and the vertical axis is frequency. The standard deviation of the distribution for the healthy individuals was σ=0.0560, and the standard deviation of the distribution for the atrial fibrillation patients was σ=0.355. As shown in FIG. 5, in the distribution for the atrial fibrillation patients, 74.6% of actually measured total frequency for the atrial fibrillation patient were distributed outside the range of ±2σ=±0.112, which is equal to twice the standard deviation for the healthy individual. Thus, it is conceivable that atrial fibrillation can be detected by designating a normal normalized heartbeat period $T_N$ for the healthy individual, and counting normalized heartbeat periods that are greater than $T_N$ among a prescribed number of beats. For example, with the normal normalized heartbeat period set to 2σ in the distribution for healthy individuals obtained previously, when the number of abnormal normalized heartbeat periods for which $|DR(2)|>T_N=0.112$ during 10 beats is counted, it can be expected that the abnormal normalized heartbeat period count for the healthy individuals will be 0, while that for the atrial fibrillation patients will be 7 (since 74.6% of the total frequency for the atrial fibrillation patient is distributed outside the range of ±2σ=±0.112, it is thought that 7 beats out of 10 will lie outside that range), and therefore atrial fibrillation can be distinguished by this method. In terms of increasing the accuracy of distinction, a large difference in the aforementioned distributions between the healthy individual and the atrial fibrillation patient is better. Accordingly, distributions of normalized heartbeat periods defined by the following equation (13) for the healthy individual and for the atrial fibrillation patient were examined.

$$DR(10)_n = \frac{10(R_{n-1} - R_n)}{\sum\limits_{k=n-9}^{n} R_k} \tag{13}$$

The standard deviation of the distribution for the healthy individuals was σ=0.0590, and the standard deviation of the distribution for the atrial fibrillation patients was σ=0.371. In the distribution for the atrial fibrillation patient, 72.0% of the actually measured total frequency for the atrial fibrillation patient was distributed outside the range of ±2σ=±0.118 for the healthy individual. This is smaller than the distribution obtained from DR(2). The normalized heartbeat period was further generalized as in the following equation (14) (the following equation (14) is the same as equation (1)), and a case in which N>10 was examined, but the trend was the same as when N=10.

$$DR(N)_n = \frac{N(R_{n-1} - R_n)}{\sum\limits_{k=n-N+1}^{n} R_k} \tag{14}$$

(N is an integer equal to 1 or greater)

Thus, for the atrial fibrillation patient, the proportion of normalized heartbeat periods that are distributed to the outside of twice the standard deviation for the healthy individual is greatest at a normalized heartbeat period of N=2, and it is therefore appropriate to employ the normalized heartbeat period DR(2) in order to distinguish between the healthy individual and the atrial fibrillation patient by counting abnormal normalized heartbeat periods; however, it is also possible to distinguish an atrial fibrillation patient by using an integer other than 2.

Therefore, the atrial fibrillation patient can be distinguished by employing the aforementioned equation (1).

Method for Detecting Atrial Fibrillation

The validity of the method of counting, from among a prescribed number of continuous normalized heartbeat periods, those having an absolute value that exceeds a prescribed normal heartbeat period threshold value, and determining atrial fibrillation to be present when the count has exceeded a prescribed normal cumulative count threshold value, will be examined.

Figure 7:
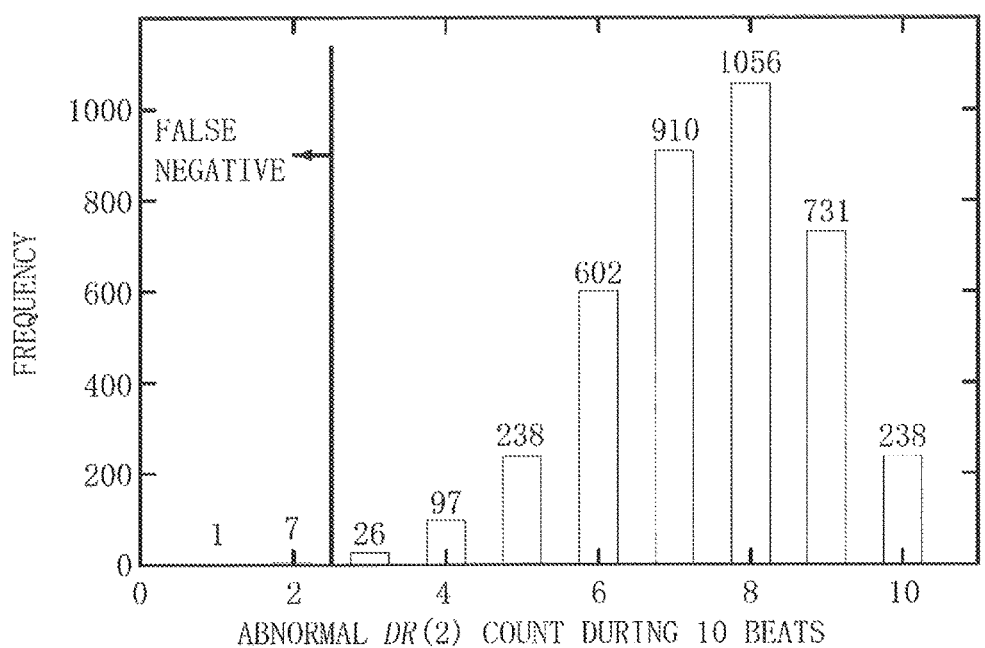
FIG. 7 is a graph showing a distribution of abnormal DR(2) count during 10 beats in an atrial fibrillation patient.

First, as one case, a case that involves adopting the normalized heartbeat period DR(2), then dividing a time series of heartbeat periods into intervals of 10 beats each, and counting the number of abnormal DR(2) for which $|DR(2)|>T_N=0.112$ that occur during these 10 beats, shall be examined. As shown in FIG. 5, for the atrial fibrillation patient, abnormal DR(2) values constituted 74.6 of the total frequency, and therefore the averaged abnormal DR(2) count in each interval is 7. For the healthy individual, on the other hand, abnormal DR(2) values are expected to be 4.55% of the total frequency, and therefore the count is thought to be about to 1. Accordingly, taking a value between 0 and 7, it was decided to make a determination of atrial fibrillation when the abnormal DR(2) count per interval is greater than 2. The abnormal DR(2) counts in each of 10-beat intervals for the healthy individual and the atrial fibrillation patient were examined; plots of the abnormal count and frequency thereof are shown respectively in FIG. 6 and FIG. 7. The horizontal axis is the abnormal DR(2) count in each interval, and the vertical axis is the frequency. When atrial fibrillation is designated as "positive" and normal (healthy individual) as "negative," as indicated in FIG. 7, for the atrial fibrillation patient, there were eight false-negative intervals in which the abnormal DR(2) count was 2 or less from among a total of 3,906 intervals, for a false-negative proportion of 0.205%. As indicated in FIG. 6, for the healthy individual, there were 67 false-positive intervals from among a total of 3,898 intervals, for a false-positive proportion of 1.72%. The frequency of an abnormal DR(2) count of 3 was particularly high; this is attributed to premature ventricular contraction. Because isolated premature ventricular contractions frequently occur in the healthy individual as well, it is necessary to consider methods for excluding these premature contractions.

Figure 8:
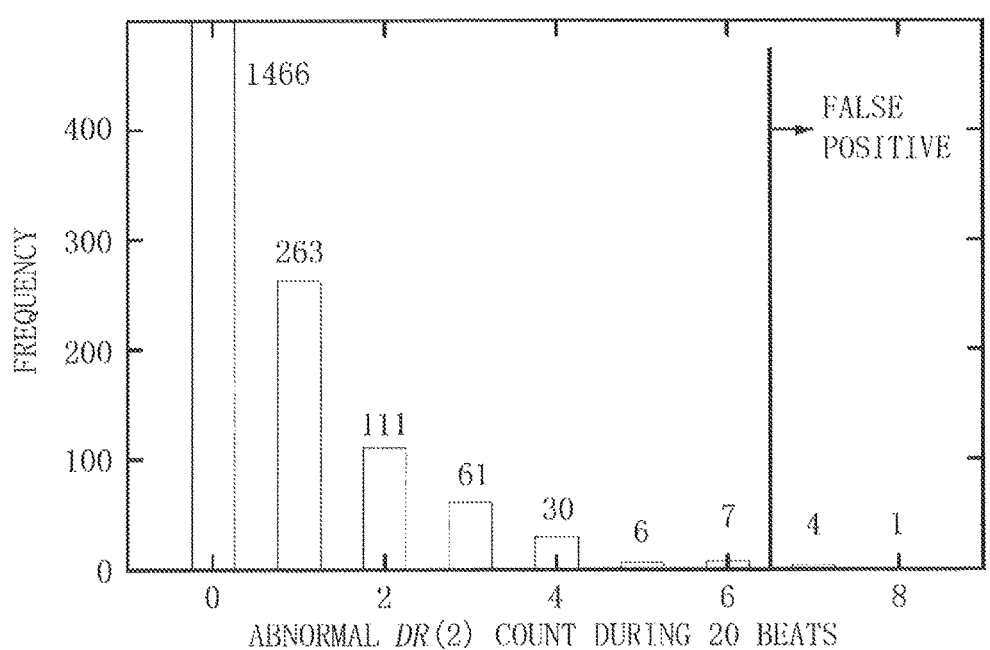
FIG. 8 is a graph showing a distribution of abnormal DR(2) count during 20 beats in a healthy individual.
Figure 9:
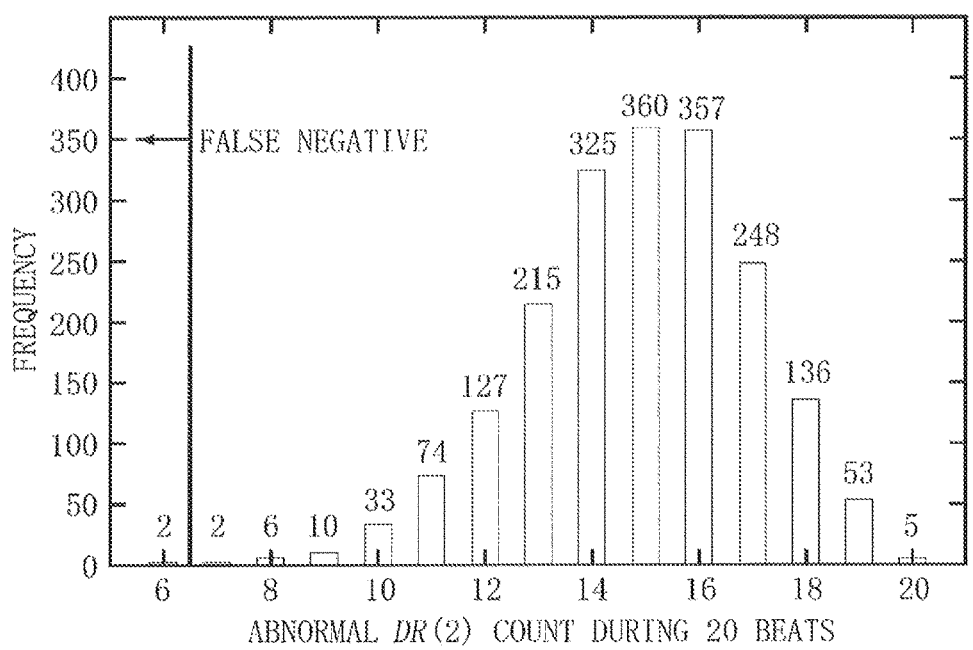
FIG. 9 is a graph showing a distribution of abnormal DR(2) count during 20 beats in an atrial fibrillation patient.

Next, an instance of adopting DR(2) as the normalized heartbeat period, dividing a time series of heartbeat periods into intervals of 20 beats each, and counting the number of abnormal DR(2) for which $|DR(2)|>T_N=0.112$ that occur during these 20 beats was examined. At this time, the abnormal DR(2) count for the atrial fibrillation patient can be expected to be about 15, while that for the healthy individual is thought to be about 1. Accordingly, taking a value between 15 and 1, it was decided to make a determination of atrial fibrillation when the abnormal DR(2) count per interval is greater than 6. The abnormal DR(2) count in each of 20-beat intervals for the healthy individual and the atrial fibrillation patient were examined; plots of the abnormal DR(2) count and frequency thereof are shown respectively in FIG. 8 and FIG. 9. As indicated in FIG. 8, for the healthy individual, there were five false-positive intervals from among a total of 1,949 intervals, for a false-positive proportion of 0.257%. As indicated in FIG. 9, for the atrial fibrillation patient, there were two false-negative intervals from among a total of 1,953 intervals, for a false-negative proportion of 0.102%. In both instances, the proportion of false-positives and false-negatives was smaller than when a time series of heartbeat periods was evaluated by division into intervals of 10 beats each. Consequently, it is suitable to employ the abnormal DR(2) count within 20 beats, to detect atrial fibrillation (i.e., it is suitable to employ the preceding equation (9)). While it is thought that employing an even greater number of heartbeats would reduce false-positives and false-negatives, if the number is too great, the inability to detect paroxysmal atrial fibrillation occurring within a short time period becomes a concern.

Verification in Individuals Having Premature Atrial Contraction

As described above, it has been shown that a determination of atrial fibrillation can be made when, using an abnormal normalized heartbeat period of $|DR(2)|>T_N=0.112$, the abnormal DR(2) count from among 20 beats is greater than 6. It was examined whether this method can be used to distinguish between premature atrial contraction and atrial fibrillation. A premature atrial contraction is a premature contractions that simply occurs one at a time in isolated fashion, and poses no health risk.

Figure 10:
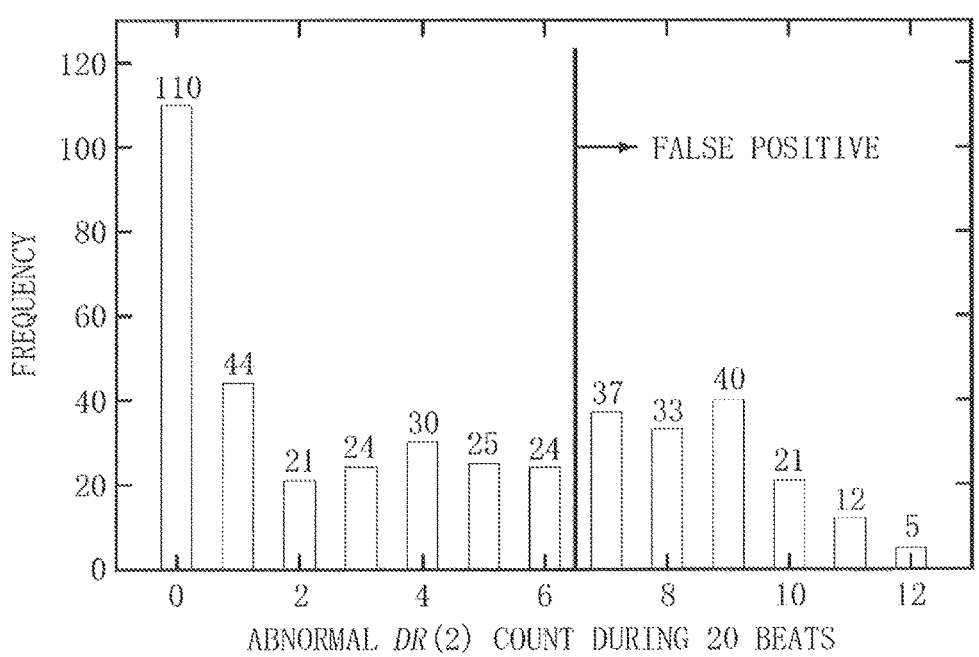
FIG. 10 is a graph showing a distribution of abnormal DR(2) count during 20 beats in an individual having premature atrial contractions.

Heartbeat periods of an individual having premature atrial contractions was monitored over a two-hour period, to investigate the abnormal DR(2) count within each of 20-beat intervals; FIG. 10 is a plot of the abnormal DR(2) count and frequency thereof. Out of a total frequency of 426 intervals, there were false-positives in 148 intervals, for a false-positive proportion of 34.7%. Under these circumstances, atrial fibrillation and premature atrial contractions posing no threat to health cannot be distinguished, and it is therefore necessary to exclude premature atrial contractions.

Exclusion of Premature Contractions

Method for Excluding Premature Ventricular Contractions

Figure 11:
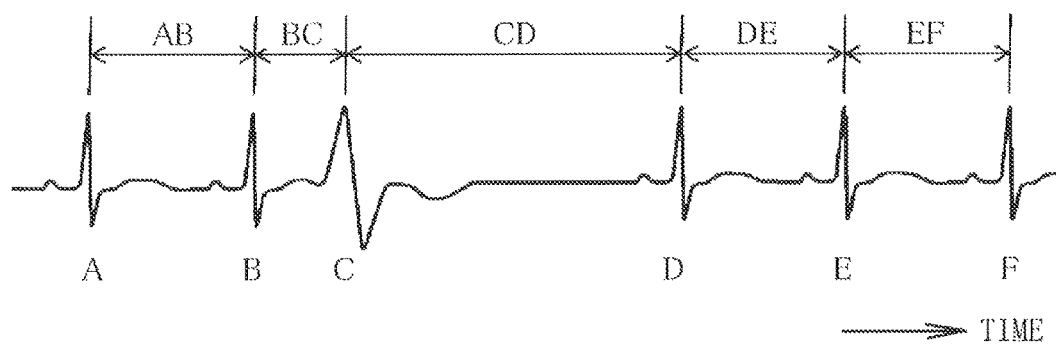
FIG. 11 is a diagrammatic illustration of a typical premature ventricular contraction electrocardiographic complex.

FIG. 11 shows an electrocardiographic complex of a typical premature ventricular contraction. In it, beat C corresponds to the premature ventricular contraction. Beat C appears earlier than would a beat produced at the sinus rate, and is followed by a return to the sinus rate with beat D. Therefore, the values of $|DR(2)|$ corresponding to the heartbeat periods BC, CD, and DE are large. This is why, in FIG. 6, intervals in which the abnormal DR(2) count per interval is 3 were so numerous.

As shown in FIG. 11, the heartbeat periods of a premature ventricular contraction have a relationship that can be approximated as $2 \times AB \approx BC+CD \approx 2 \times DE$, and that generally satisfies the equation $0.75 \times AB > BC$. Accordingly, in order to exclude normalized heartbeat periods that relate to premature ventricular contractions, which may take on abnormal values, a location that corresponds to the following equations (15) and (16) is retrieved from a time series of heartbeat periods (the following equations (15) and (16) are respectively the same as equation (2) and equation (3)).

$$|DR(N)_i| > T_p \qquad (15)$$

$$\frac{|R_i + R_{i+1} - 2\overline{R}_{i-1}(M)|}{2\overline{R}_{i-1}(M)} < 2T_N \qquad (16)$$

Here, R is the heartbeat period, $T_p$ and $T_N$ are prescribed threshold values that satisfy the relationships $T_p>0$ and $T_N>0$, subscript i is a time series, and i signifies the past with respect to i+1. The retrieved $R_i$ corresponds to the heartbeat period BC in FIG. 11. When X is an integer equal to 1 or greater, $R_i$ bar (X) is represented by the following equation (17) (the following equation (17) is the same as equation (4)).

$$\bar{R}_i(X) = \frac{1}{X} \sum_{k=i-X+1}^{i} R_k \quad (17)$$

M is an integer equal to 1 or greater. When the location in question has been detected, $DR(N)_i$ and the two values $DR(N)_{i+1}$ and $DR(N)_{i+2}$ successive thereto are excluded.

In view of the nature of the premature ventricular contraction, the threshold value $T_p$ is appropriately 0.2-0.3, and more preferably 0.25. Typically, fluctuations of the heartbeat periods of a healthy individual will be within about 10%, and therefore the most appropriate threshold value $T_N$ for identifying abnormal heartbeat periods is 0.1. While the parameter M may be any value, exclusion capability is sufficient even when M=1, and considering that the amount of computation required is less than when M>1, this value is the most appropriate.

Here, a case in which $T_p$=0.25, $T_N$=0.1, N=2, and M=1 will be described, taking the example of FIG. 11. Where $R_i$ is BC, the preceding equation (15) can be written as in the following equation (18). The preceding equation (16) can be written as in the following equation (19).

$$\frac{2|AB - BC|}{AB + BC} > 0.25 \quad (18)$$

$$\frac{|BC + CD - 2AB|}{2AB} < 0.2 \quad (19)$$

To satisfy equation (18) and equation (19), the normalized heartbeat periods $DR(2)_i$, $DR(2)_{i+1}$ and $DR(2)_{i+2}$, which correspond to the heartbeat periods BC, CD, and DE, are excluded. Positing a premature ventricular contraction heartbeat period time series in which, for example, the heartbeat period values in FIG. 11 are such that AB=DE=1,000 ms, BC=700 ms, and CD=1,300 ms, the left term of equation (18) is 0.353, and the left term of equation (19) is 0, and both equations are satisfied. The normalized heartbeat period $DR(2)_i$ which corresponds to the heartbeat period value BC at this time, when converted using equation (9), is 2(1,000−700)/(1,000+700)=0.353, and likewise the normalized heartbeat periods $DR(2)_{i+1}$ and $DR(2)_{i+2}$ which correspond to CD and DE are respectively −0.600 and 0.261; therefore, if $|DR(2)|>T_N$ is selected as the abnormal normalized heartbeat period, the normalized heartbeat periods $DR(2)_i$, $DR(2)_{i+1}$ and $DR(2)_{i+2}$ will be determined to be abnormal normalized heartbeat periods due to premature ventricular contraction, and must therefore be excluded.

Consequently, abnormal normalized heartbeat periods produced in the method mentioned above due to a premature ventricular contraction can be retrieved and excluded.

Method for Excluding Premature Atrial Contractions

Figure 12:
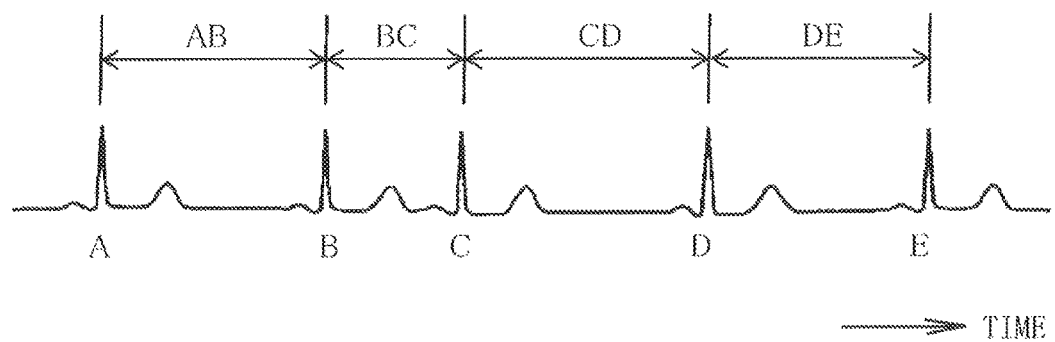
FIG. 12 is a diagrammatic illustration of a typical premature atrial contraction electrocardiographic complex.

FIG. 12 shows an electrocardiographic complex of a typical premature atrial contraction. In it, beat C corresponds to the premature atrial contraction. Beat C appears early or irregularly, and is followed by a return to the normal sinus rate with beat D. While the premature atrial contraction is isolated, with higher frequency of occurrence, the normalized heartbeat periods corresponding to the heartbeat periods BC and CD will take on abnormal values, thereby producing a false-positive as shown in FIG. 10. As shown in FIG. 12, the heartbeat periods of the premature atrial contraction generally have a relationship such that AB>BC, CD>BC, and AB≈CD. To exclude normalized heartbeat periods that relate to premature atrial contractions, which may take on abnormal values, a location that corresponds to the following equations (20) and (21) is retrieved from a time series of heartbeat periods (the following equations (20) and (21) are respectively the same as equation (5) and equation (8)).

$$\frac{R_i + R_{i+1} - 2\bar{R}_{i-1}(M)}{2\bar{R}_{i-1}(M)} < 2T_A \quad (20)$$

$$\frac{(K+1)|R_{i-1} - R_{i+1}|}{K\bar{R}_{i-1}(K) + R_{i+1}} < T_N \quad (21)$$

Here, $R_i$ bar (X) is equation (17) (equation (17) is the same as equation (7)), and when X=0, is represented by the following equation (22) (equation (22) is the same as equation (8)).

$$\bar{R}_i(0) = 0 \quad (22)$$

The retrieved $R_i$ corresponds to the heartbeat period BC in FIG. 12. $T_N$>0; $T_A$ is a prescribed threshold value that, due to the nature of premature atrial contractions, satisfies the condition $-T_N \leq T_A \leq 0$; subscript i is a time series; and i signifies the past with respect to i+1. M is an integer equal to 1 or greater, and K is an integer equal to 0 or greater. When the location in question has been detected, $DR(N)_i$ and the value $DR(N)_{i+1}$ successive thereto are excluded.

As stated previously, as fluctuations of the heartbeat periods of the healthy individual are within about 10%, the most appropriate threshold value $T_N$ is 0.1. While the exclusion capability is highest when the threshold value $T_A$ is 0, in consideration of the fact that the beat of a premature atrial contraction appears early to an extent that exceeds fluctuations in the heartbeat period of the healthy individual, the exclusion capability is sufficient even when $T_A = T_N$. For the parameters M and K, the exclusion capability is sufficient even when M=K=1, and considering that the amount of computation required is less than when M>1 or K>1, this value is the most appropriate.

Here, a case in which $T_N$=0.1, $T_A$=0, M=K=1, and N=2, will be described, taking the example of FIG. 12. Where $R_i$ is BC, the preceding equation (20) can be written as in the following equation (23). The preceding equation (21) can be written as in the following equation (24).

$$BC + CD < 2AB \quad (23)$$

$$\frac{2|AB - CD|}{AB + CD} < 0.1 \quad (24)$$

To satisfy equation (23) and equation (24), the normalized heartbeat periods $DR(2)_i$ and $DR(2)_{i+1}$ which correspond to the heartbeat periods BC and CD are excluded. Positing a premature atrial contraction heartbeat period time series in which, for example, the heartbeat period values in FIG. 12 are such that AB=CD=1,000 ms and BC=700 ms, equation (23) is 1,700<2,000, and the left term of equation (24) is 0, so both equations are satisfied. The normalized heartbeat period $DR(2)_i$ which corresponds to the heartbeat period value BC at this time, when converted using equation (9), is 2(1,000−700)/(1,000+700)=0.353, and likewise the normalized heartbeat period $DR(2)_{i+1}$ which corresponds to CD is −0.353; therefore, if $|DR(2)|>T_N$ is selected as the abnormal normalized heartbeat period, the normalized heartbeat periods $DR(2)_i$ and $DR(2)_{i+1}$ will be determined to be abnormal normalized heartbeat periods, due to the premature atrial contraction, and must therefore be excluded.

Consequently, abnormal normalized heartbeat periods produced in the method mentioned above due to a premature atrial contraction can be retrieved and excluded.

Verification of Effect of Excluding Premature Contractions

Effect of Excluding Premature Vascular Contractions

Figure 13:
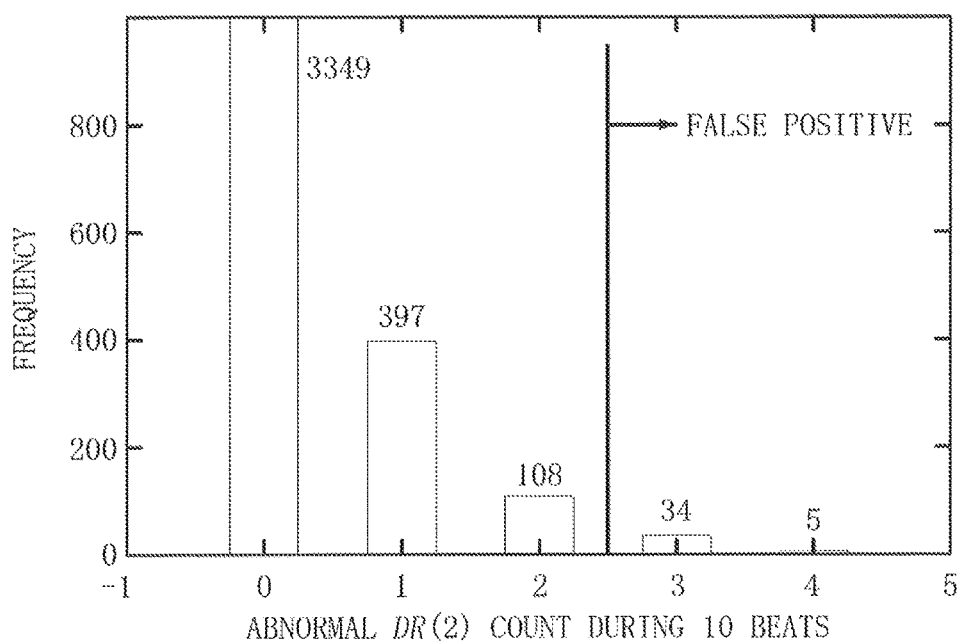
FIG. 13 is a graph showing a distribution of abnormal DR(2) count during 10 beats in a healthy individual, after elimination of premature ventricular contractions.

In order to confirm the effect of excluding premature vascular contractions, verification was carried out by the same method as that used to obtain FIG. 6 by employing heartbeat periods subsequent to exclusion of the premature vascular contractions. The premature vascular contraction exclusion parameter was $T_p=0.25$, and $T_N$ was $T_N=0.1$. To harmonize conditions, an abnormal normalized heartbeat period of DR(2)>0.112 was selected. The results are shown in FIG. 13. Of a total frequency of 3,893 intervals, 39 intervals were false-positive, for a false-positive proportion of 1.00%. This is an improvement compared to the 1.72% observed prior to exclusion of premature vascular contractions, and therefore exclusion of premature vascular contractions can be considered effective. However, this proportion is large in comparison with the false-positive rate of 0.257% obtained in the case of evaluation using 20 beats, as shown in FIG. 8. Consequently, it is considered acceptable to employ the abnormal DR(2) count during 20 beats, in order to detect atrial fibrillation.

Effect of Excluding Premature Atrial Contractions

Figure 14:
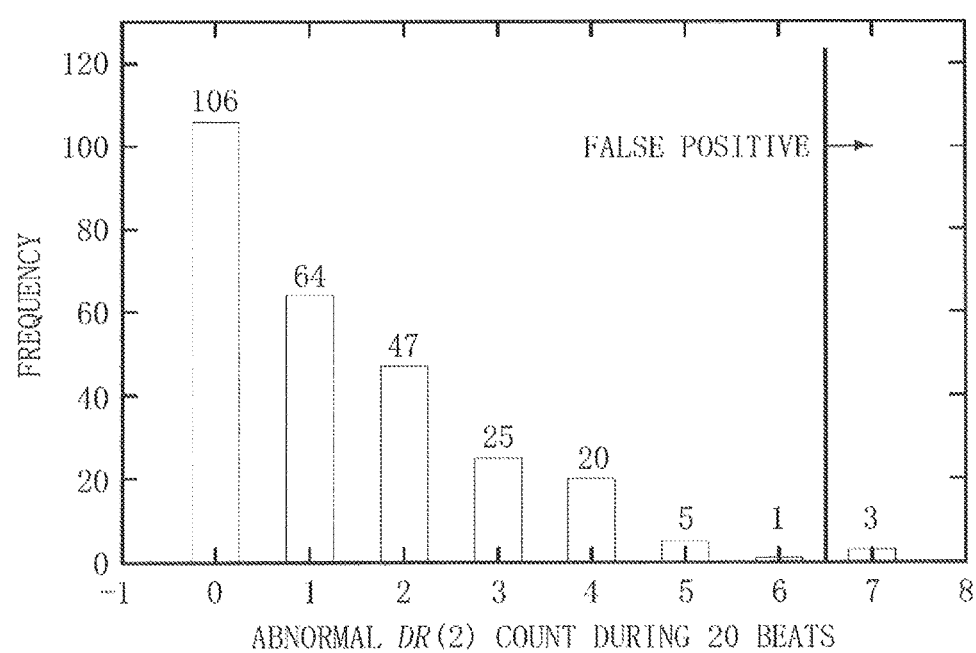
FIG. 14 is a graph showing a distribution of abnormal DR(2) count during 20 beats in an individual having premature atrial contractions, after elimination of premature atrial contractions.

For the one individual having premature atrial contractions mentioned previously, after carrying out a process to exclude the premature atrial contractions, a time series of heartbeat periods was divided into intervals of 20 beats each, and the count of abnormal normalized heartbeat periods in each interval was examined. For this verification, a normalized heartbeat period DR(2) with parameter N set to N=2 was employed. $T_N$ was set to $T_N=0.1$. That is, the abnormal normalized heartbeat period is such that |DR(2)|>0.1. The parameters of the filter needed in equation (21) and equation (22) were set to M=K=1, and the threshold value $T_A$ was set to $T_A=0$. The abnormal DR(2) count and frequency thereof for each 20-beat interval are plotted in FIG. 14. Of a total frequency of 271 intervals, 3 intervals were false-positive, for a false-positive proportion of 0.011%. This is much smaller in comparison with the proportion of 34.7% observed prior to exclusion of premature atrial contractions, and shows that the premature atrial contraction exclusion method discussed above is effective.

Comprehensive Verification Including Exclusion of Premature Contractions

Using a normalized heartbeat period DR(2), after excluding premature atrial contractions and premature ventricular contractions, a time series of heartbeat periods was divided into intervals of 20 beats each, deeming atrial fibrillation to have occurred when the abnormal normalized heartbeat period exceeded 6 within this 20-beat interval. The normal normalized heartbeat period was $T_N=0.1$, and the abnormal normalized heartbeat period was |DR(2)|>$T_N$. The premature atrial contraction exclusion parameters were M=K=1, and the threshold value $T_A$ was $T_A=0$. The premature ventricular contraction exclusion parameter was $T_p=0.25$.

Figure 15:
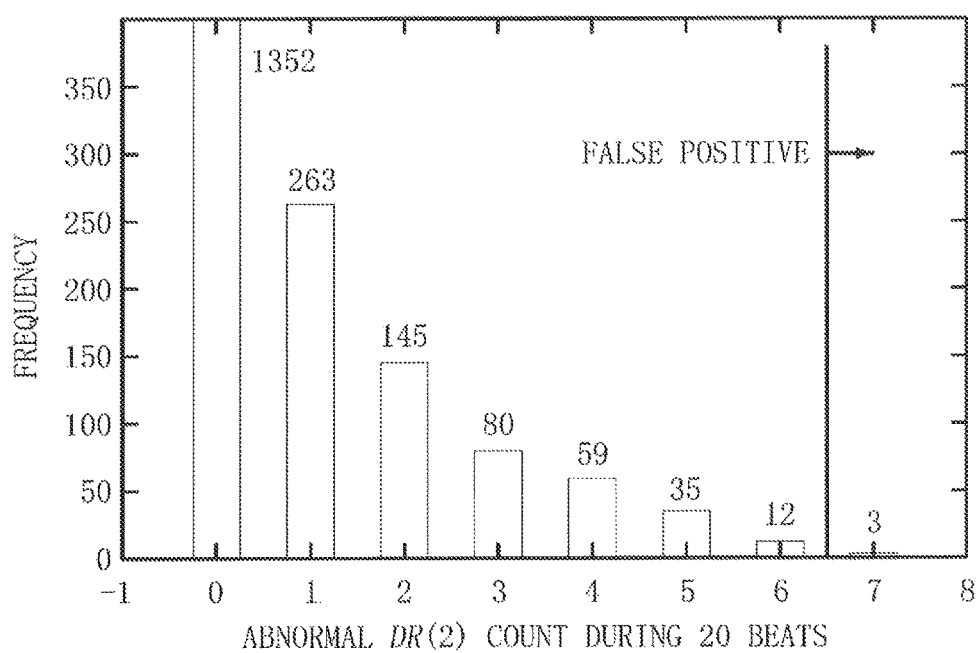
FIG. 15 is a graph showing a distribution of abnormal DR(2) count during 20 beats in a healthy individual, after elimination of premature atrial and ventricular contractions.
Figure 16:
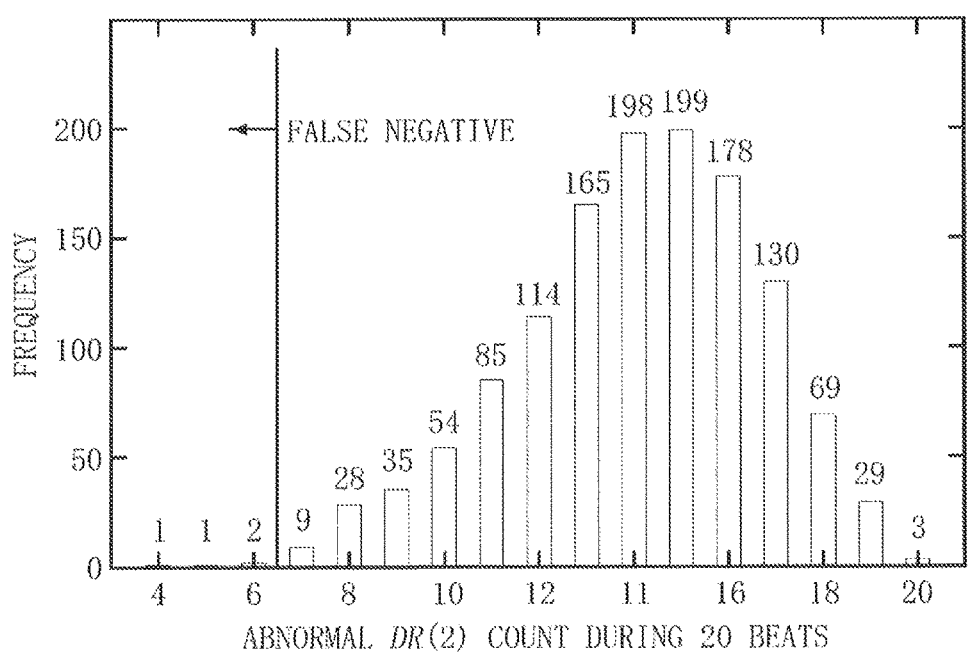
FIG. 16 is a graph showing a distribution of abnormal DR(2) count during 20 beats in an atrial fibrillation patient, after elimination of premature atrial and ventricular contractions.

Abnormal normalized heartbeat period distributions respectively obtained from heartbeat periods of four healthy individuals and five atrial fibrillation patients over a two-hour period are shown in FIG. 15 and FIG. 16. In FIG. 15, with the healthy individuals, 3 intervals among a total frequency of 1,949 intervals were false-positive, for a false-positive proportion of 0.154%. In FIG. 16, with the atrial fibrillation patients, 4 intervals among a total frequency of 1,300 intervals were false-negative, for a false-negative proportion of 0.308%. Therefore, the method employing the aforementioned equations (1) to (9) can be considered as satisfactory for detecting atrial fibrillation from heartbeat periods.

The invention claimed is:

1. An atrial fibrillation detection system for detecting the presence of atrial fibrillation in a subject, wherein the atrial fibrillation detection system comprises:
   a sensor comprising heartbeat period measurement means that measures heartbeat periods of the heart;
   a storage for storing a normal heartbeat period value and a normal cumulative count threshold value;
   a processor comprising:
      a normalized heartbeat period computation means that computes normalized heartbeat periods DR(N) represented by equation (1), $$DR(N)_n = \frac{N(R_{n-1} - R_n)}{\sum_{k=n-N+1}^{n} R_k} \quad (1)$$

where $R_n$ is a time series of heartbeat periods of the heart, from heartbeat periods of the heart that were measured by the heartbeat period measurement means, N is an integer equal to or greater than 2, subscript n is a time series, and n signifies the past with respect to n+1;
      an abnormal normalized heartbeat period cumulation means that, from among a prescribed number of successive normalized heartbeat periods DR(N), determines an absolute value of each heartbeat period of the normalized heartbeat periods, and adds up a count of abnormal normalized heartbeat periods that have an absolute value exceeding the normal heartbeat period value; and
      a comparison/determination means that compares the cumulative count of the abnormal normalized heartbeat periods and the normal cumulative count threshold value, and in the event that the cumulative count of the abnormal normalized heartbeat periods exceeds the normal cumulative count threshold value, determines that atrial fibrillation has occurred, and
   a communicator for communicating to a user that atrial fibrillation has occurred.

2. The atrial fibrillation detection system according to claim 1, wherein the atrial fibrillation detection system comprises a premature ventricular contraction exclusion means that excludes from the normalized heartbeat periods those normalized heartbeat periods that relate to premature ventricular contractions.

3. The atrial fibrillation detection system according to claim 2, wherein the premature ventricular contraction exclusion means is configured to exclude normalized heartbeat periods that relate to premature ventricular contractions, by:
   from among the normalized heartbeat periods DR(N)$_i$ from a time series R$_i$ of heartbeat periods of the heart, retrieving a normalized heartbeat period DR(N)$_i$ that satisfies equations (2) and (3),
   subsequently excluding DR(N)$_i$ and two values DR(N)$_{i+1}$ and DR(N)$_{i+2}$ successive thereto from the retrieved normalized heartbeat period DR(N)$_i$, $$|DR(N)_i| > T_P \quad (2)$$

$$\frac{|R_i + R_{i+1} - 2\overline{R}_{i-1}(M)|}{2\overline{R}_{i-1}(M)} < 2T_N \quad (3)$$

wherein $T_P$ and $T_N$ are prescribed threshold values that satisfy the relationships $T_P>0$ and $T_N>0$, subscript i is a time series, and i signifies the past with respect to i+1, wherein $R_i$ bar (X) in equation (3) is represented by equation (4), $$\overline{R}_i(X) = \frac{1}{X} \sum_{k=i-X+1}^{i} R_k \quad (4)$$

and wherein M and X are integers equal to 1 or greater.

4. The atrial fibrillation detection system according to claim 3, wherein the atrial fibrillation detection system comprises a premature atrial contraction exclusion means that excludes from the normalized heartbeat periods those normalized heartbeat periods that relate to premature atrial contractions.

5. The atrial fibrillation detection system according to claim 4, wherein the premature atrial contraction exclusion means is configured to exclude normalized heartbeat periods that relate to premature atrial contractions, by:
from among the normalized heartbeat periods $DR(N)_i$ from a time series Ri of heartbeat periods of the heart, retrieving a normalized heartbeat period $DR(N)_i$ that satisfies the following equations (5) and (6),
subsequently excluding $DR(N)_i$ and the value $DR(N)_{i+1}$ successive thereto from the retrieved normalized heartbeat period $DR(N)_i$, $$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

wherein $T_N$ and $T_A$ are prescribed threshold values that satisfy the relationships $T_N>0$ and $-T_N \leq T_A \leq 0$, subscript i is a time series, and i signifies the past with respect to i+1,
wherein M is an integer equal to 1 or greater, and K is an integer equal to 0 or greater,
and wherein $R_i$ bar (X) in equations (5) and (6) is represented by equation (7):

$$\overline{R}_i(X) = \frac{1}{X} \sum_{k=i-X+1}^{i} R_k \quad (7)$$

when X is an integer equal to 1 or greater, and by equation (8):

$$\overline{R}_i(0) = 0 \quad (8)$$

when X=0.

6. The atrial fibrillation detection system according to claim 2, wherein the atrial fibrillation detection system comprises a premature atrial contraction exclusion means that excludes from the normalized heartbeat periods those normalized heartbeat periods that relate to premature atrial contractions.

7. The atrial fibrillation detection system according to claim 6, wherein the premature atrial contraction exclusion means is configured to exclude normalized heartbeat periods that relate to premature atrial contractions, by:
from among the normalized heartbeat periods $DR(N)_i$ from a time series Ri of heartbeat periods of the heart, retrieving a normalized heartbeat period $DR(N)_i$ that satisfies the following equations (5) and (6),
subsequently excluding, $DR(N)_i$ and the value $DR(N)_{i+1}$ successive thereto from the retrieved normalized heartbeat period $DR(N)_i$, $$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

wherein $T_N$ and $T_A$ are prescribed threshold values that satisfy the relationships $T_N>0$ and $-T_N \leq T_A \leq 0$, subscript i is a time series, and i signifies the past with respect to i+1,
wherein M is an integer equal to 1 or greater, and K is an integer equal to 0 or greater,
wherein $R_i$ bar (X) in equations (5) and (6) is represented by equation (7):

$$\overline{R}_i(X) = \frac{1}{X} \sum_{k=i-X+1}^{i} R_k \quad (7)$$

when X is an integer equal to 1 or greater, and by equation (8):

$$\overline{R}_i(0) = 0 \quad (8)$$

when X=0.

8. The atrial fibrillation detection system according to claim 1, wherein the atrial fibrillation detection system comprises a premature atrial contraction exclusion means that excludes from the normalized heartbeat periods those normalized heartbeat periods that relate to premature atrial contractions.

9. The atrial fibrillation detection system according to claim 8, wherein the premature atrial contraction exclusion means is configured to exclude normalized heartbeat periods that relate to premature atrial contractions, by:
from among the normalized heartbeat periods $DR(N)_i$ from a time series Ri of heartbeat periods of the heart, retrieving a normalized heartbeat period $DR(N)_i$ that satisfies the following equations (5) and (6),
subsequently excluding, $DR(N)_i$ and the value $DR(N)_{i+1}$ successive thereto from the retrieved normalized heartbeat period $DR(N)_i$, $$\frac{R_i + R_{i+1} - 2\overline{R}_{i-1}(M)}{2\overline{R}_{i-1}(M)} < 2T_A \quad (5)$$

$$\frac{(K+1)|R_{i-1} - R_{i+1}|}{K\overline{R}_{i-1}(K) + R_{i+1}} < T_N \quad (6)$$

wherein $T_N$ and $T_A$ are prescribed threshold values that satisfy the relationships $T_N>0$ and $-T_N \leq T_A \leq 0$, subscript i is a time series, and i signifies the past with respect to i+1, wherein M is an integer equal to 1 or greater, and K is an integer equal to 0 or greater, and wherein $R_i$ bar (X) in equations (5) and (6) is represented by equation (7):

$$\overline{R}_i(X) = \frac{1}{X} \sum_{k=i-X+1}^{i} R_k \quad (7)$$

when X is an integer equal to 1 or greater, and by equation (8):

$$\overline{R}_i(0) = 0 \quad (8)$$

when X=0.

10. The atrial fibrillation detection system according to claim 1, wherein the normalized heartbeat period computation means is configured to compute a normalized heartbeat period $DR(2)_n$, represented by equation (9):

$$DR(2)_n = \frac{2(R_{n-1} - R_n)}{R_{n-1} + R_n} \quad (9)$$

from the heartbeat periods.

11. The atrial fibrillation detection system according to claim 10, wherein the sensor comprises a heartbeat period storage means for storing heartbeat periods measured by the heartbeat period measurement means, or comprises a heartbeat period transmission means for transmitting to the processor the measured heartbeat periods, the system being configured such that atrial fibrillation is detected by inputting the heartbeat periods measured using the sensor to the processor via the heartbeat period storage means or the heartbeat period transmission means.

12. The atrial fibrillation detection system according to claim 1, wherein the sensor comprises a heartbeat period storage means for storing heartbeat periods measured by the heartbeat period measurement means, or comprises a heartbeat period transmission means for transmitting to the processor the measured heartbeat periods, the system being configured such that atrial fibrillation is detected by inputting the heartbeat periods measured using the sensor to the processor via the heartbeat period storage means or the heartbeat period transmission means.

13. The atrial fibrillation detection system according to claim 1, wherein the communicator comprises at least one of a display, an LED, a speaker, a buzzer, an earphone, or a vibrator.

14. The atrial fibrillation detection system according to claim 13, wherein the communicator comprises the display.

15. The atrial fibrillation detection system according to claim 13, wherein the communicator comprises the LED.

16. The atrial fibrillation detection system according to claim 13, wherein the communicator comprises the speaker.

17. The atrial fibrillation detection system according to claim 13, wherein the communicator comprises the earphone.

18. The atrial fibrillation detection system according to claim 13, wherein the communicator comprises the vibrator.

* * * * *